United States Patent (10) Patent No.: US 9,010,203 B2
Rabaud et al. (45) Date of Patent: Apr. 21, 2015

(54) APPARATUS AND METHOD FOR EXAMINING THE INTERNAL WALL OF A PORTION OF A TUBE, PARTICULARLY FOR EVALUATING THE EXTENT OF DEGRADATION OF A PLASTIC TUBE

(75) Inventors: Benjamin Rabaud, Sartrouville (FR); Karl Glucina, Maurecourt (FR); Christophe Cochennec, Courdimanche (FR)

(73) Assignee: R+I Alliance (FR)

( * ) Notice: Subject to any disclaimer, the term of this patent is extended or adjusted under 35 U.S.C. 154(b) by 396 days.

(21) Appl. No.: 13/516,023

(22) PCT Filed: Dec. 16, 2010

(86) PCT No.: PCT/IB2010/055866
§ 371 (c)(1),
(2), (4) Date: Sep. 25, 2012

(87) PCT Pub. No.: WO2011/073936
PCT Pub. Date: Jun. 23, 2011

(65) Prior Publication Data
US 2013/0014599 A1 Jan. 17, 2013

(30) Foreign Application Priority Data

Dec. 18, 2009 (FR) ...................................... 09 06161

(51) Int. Cl.
*B29C 67/00* (2006.01)
*G01N 21/95* (2006.01)
*G01N 21/954* (2006.01)

(52) U.S. Cl.
CPC ............ *G01N 21/95* (2013.01); *B29C 67/0018* (2013.01); *B29K 2023/06* (2013.01); *G01N 21/954* (2013.01)

(58) Field of Classification Search
CPC ... G01N 17/008; B29C 53/08; B29C 67/0018
See application file for complete search history.

(56) References Cited

U.S. PATENT DOCUMENTS 1,505,141 A 8/1924 Hawkinson
2,748,829 A 6/1956 Korenak

OTHER PUBLICATIONS

Rozenthal-Evesque, M., et al., "The NOL Ring Test an Improved Tool for Characterising the Mechanical Degradation of Non-Failed Polyethylene Pipe House Connections", Proceedings of the Plastics pipes XIV Conference, (2008), pp. 1-10.
Chung, S., et al., "An Examination of Field Failures of Plastic Piping System Components in Potable Water Applications", Proceedings of the Antec Conference, (2007), pp. 1-5.

*Primary Examiner* — Paul West
(74) *Attorney, Agent, or Firm* — The Belles Group, P.C.

(57) ABSTRACT

Apparatus for examining the internal wall of a tube by turning back a portion of a tube the cross section of which is open along an arch of circumference, particularly over approximately one quarter of a circumference, comprising: two adjacent parallel bars (3a, 3b), which are mounted such that they can slide in a structure (2) and which can be moved within their plane, about which bars the concave side of the open portion (1) of the tube can be engaged, with the geometric axis of the tube parallel to the bars; a pushing means (P) for pushing in a direction substantially orthogonal to the mean plane of the bars and capable of coming to rest against the exterior convex region of the tube portion (1); and a parting means (9) capable of spacing the bars apart in response to the pushing thrust applied to the convex region of the tube portion, the whole assembly being designed to allow the portion of the tube to be turned back on each side of the pushing region.

12 Claims, 4 Drawing Sheets

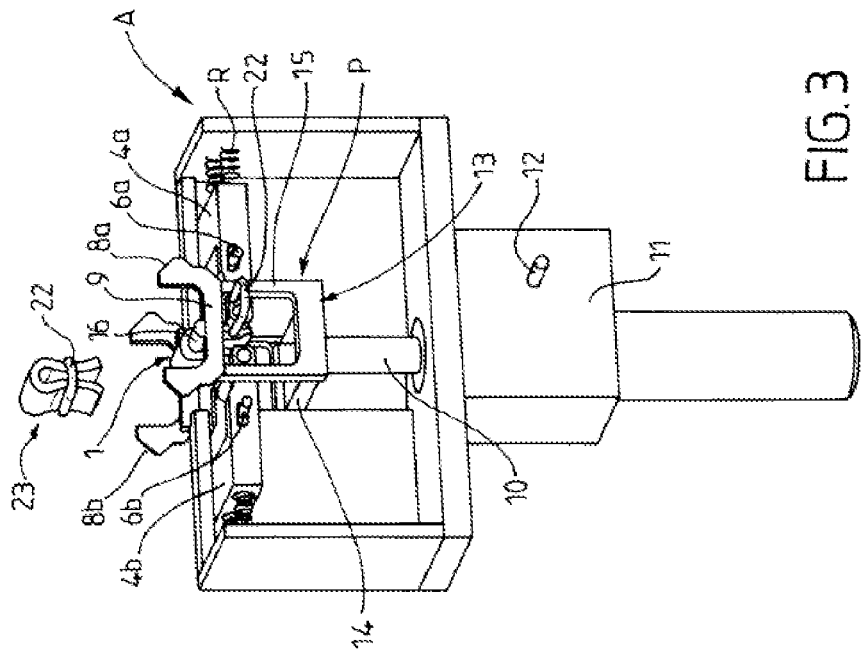
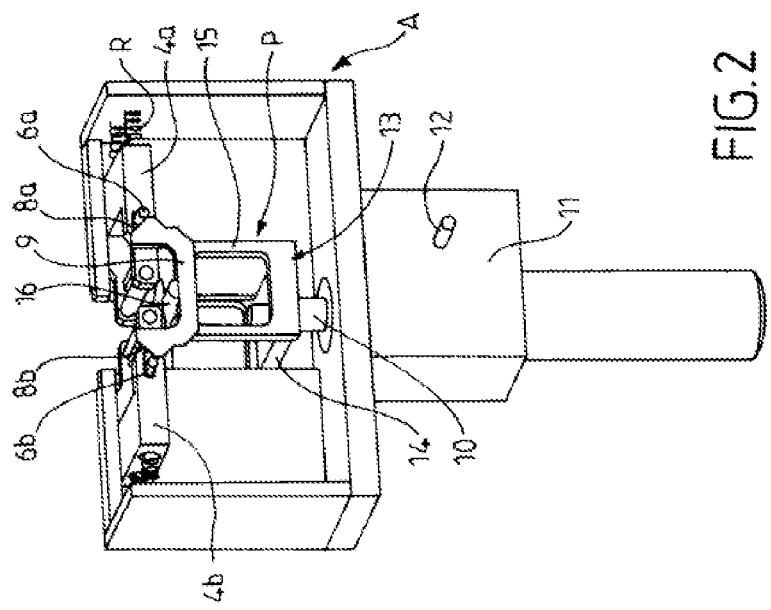

ion to the pushing against the convex area of the tube portion, wherein the tube portion may be turned completely inside out on either side of the pushing area.

The pusher means advantageously comprise, in order to come into contact with the tube portion, an interchangeable cylindrical element having a geometrical axis parallel to the bars, disposed on the convex side of the tube portion opposite the bars, the cylindrical element being carried at each end by a pusher moved by a rod.

The diameter of the cylindrical element is advantageously at least equal to the thickness of the tube portion to be turned inside out. The length of the cylindrical element is at least substantially equal to that of the bars.

The pusher means preferably comprise a force amplifier for moving the cylindrical element against the tube portion. This force amplifier may be actuated manually or by an electric motor.

The means for moving the bars apart may comprise a double cam adapted to cooperate with a sliding support associated with each bar, this cam being moved by the pusher to cause the bars to be moved apart when pushed.

The apparatus advantageously includes a mobile observation device with optical magnification means, in particular an eyepiece with a counting square, for observing the internal surface of the tube portion turned inside out.

The observation device may include a digital camera preferably connected to image processing means with software adapted to determine a degree of deterioration of the tube.

The invention also relates to a method of analyzing the level of deterioration of a plastic material, notably polyethylene, tube, wherein a tube portion is taken from which an arc of its circumference is removed to open the section, characterized in that the open portion of the tube is turned inside out by apparatus as defined above and the internal wall of the area turned inside out is observed to determine the level of deterioration of the tube.

The tube portion is preferably turned inside out at a constant speed of movement of the pusher means.

In the case of a black polyethylene tube, a visual assessment of the deterioration may be effected according to a nomogram constituted by a set of reference representations of tube portions turned inside out corresponding to various levels of deterioration.

The invention also relates to a nomogram for implementation of the method as defined above, characterized in that it is constituted by a set of reference representations of tube portions turned inside out by apparatus as defined above and corresponding to various levels of deterioration.

Apart from the features described above, the invention consists in a number of other features addressed more explicitly hereinafter apropos embodiments that are described with reference to the appended drawings but are in no way limiting on the invention. In the drawings:

FIG. 2 is a view to a smaller scale and from a different angle than FIG. 1 of the apparatus at the beginning of pushing and spreading the bars, the large front face of the frame having been removed to make the diagram easier to read.

FIG. 3 shows, in a similar way to FIG. 2, the apparatus at the end of pushing and of turning inside out the tube portion with, above it, a portion of tube turned inside out and extracted from the apparatus.

APPARATUS AND METHOD FOR EXAMINING THE INTERNAL WALL OF A PORTION OF A TUBE, PARTICULARLY FOR EVALUATING THE EXTENT OF DEGRADATION OF A PLASTIC TUBE

PRIORITY

Priority is claimed as a national stage application, under 35 U.S.C. §371, to PCT/IB2010/055866, filed Dec. 16, 2010, which claims priority to French Application No. 09/06161, filed Dec. 18, 2009. The disclosures of the aforementioned priority applications are incorporated herein by reference in their entirety.

The invention relates to apparatus for examining the internal wall of a tube by turning inside out a tube portion the section of which is open over an arc of its circumference, in particular over approximately a quarter of its circumference.

The invention relates more particularly, but not exclusively, to such apparatus for characterizing the deterioration of plastic material tubes, notably polyethylene tubes, even more particularly polyethylene tubes used in drinking water distribution networks.

The use of plastic materials, and notably polyethylene, for the production or refurbishing of drinking water distribution networks has increased considerably in recent years. Polyethylene pipes have numerous advantages: ease of use, better resistance to corrosion than metal pipes, attractive cost.

However, in the past few years, premature cracking of polyethylene pipes has occurred, notably in networks where final disinfection is effected using chlorine dioxide. Research has shown that these cracks were the result of premature deterioration of the internal wall of the pipes concerned. The deterioration is caused by oxidation of the polyethylene in contact with the water. This oxidation leads to the appearance of microcracks, some of which can extend through the wall and emerge on the outside.

A number of experimental laboratory techniques exist for quantifying the deterioration of the polyethylene.

In particular, one experimental laboratory test consists in turning inside out a tube portion the section of which is open over an arc of its circumference to examine the area turned inside out and the possible presence of tears or separation of material manifesting in the form of cracks.

This turning inside out method of examining tubes is particularly recommended for polyethylene tubes, but may be applied to tubes produced in other plastic material.

The main object of the invention is to provide apparatus enabling rapid and reproducible execution of the operation of turning inside out the tube portion either in a laboratory or in the field. To this end the apparatus must be relatively light in weight and easy to use.

Figure 4:
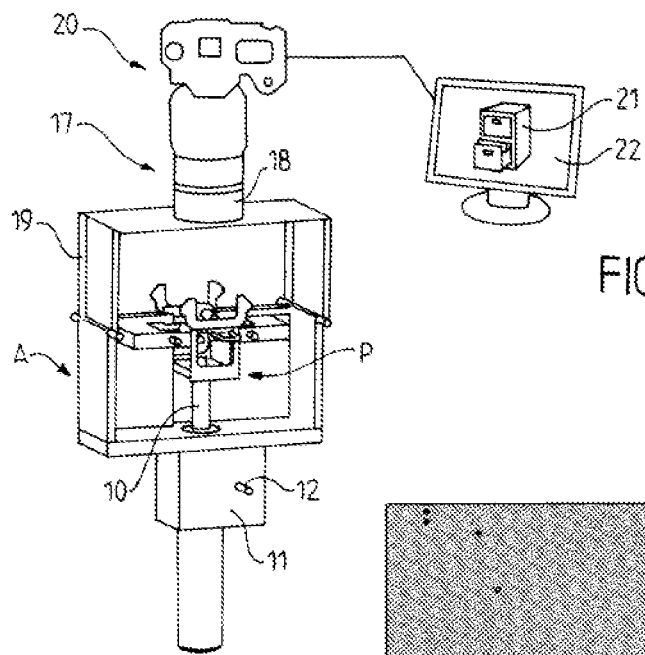

According to the invention, apparatus for the examination of the internal wall of a tube by turning inside out a tube portion the section of which is open over an arc of its circumference, in particular over approximately a quarter of its circumference, is characterized in that it includes:

two adjacent parallel bars, mounted to slide in a frame and adapted to be moved in their plane, around which bars may be engaged the concave side of the open portion of the tube, with its geometrical axis parallel to the bars, pusher means for pushing in a direction substantially orthogonal to the mean plane of the bars, adapted to come to bear against the exterior convex area of the tube portion, and FIG. 4 shows in perspective, to a smaller scale, the apparatus surmounted by an observation device consisting of a digital camera connected to an image processing unit.

Figure 5:
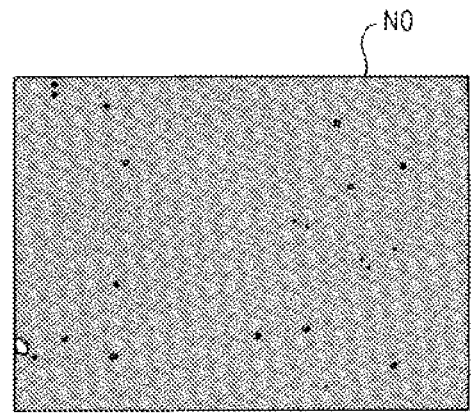

FIG. 5 is a representation of an internal surface portion of a black polyethylene tube with no deterioration.

Figure 6:
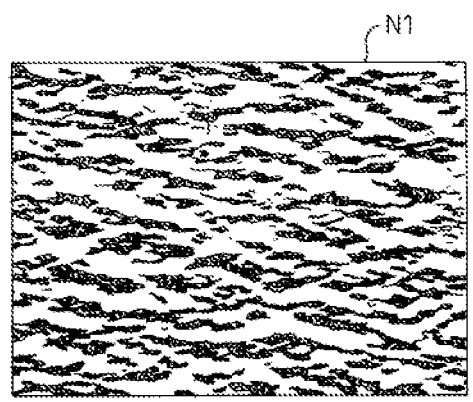

FIG. 6 shows, in a similar way to FIG. 5, a portion of the internal surface of a tube with a low level of deterioration.

Figure 7:
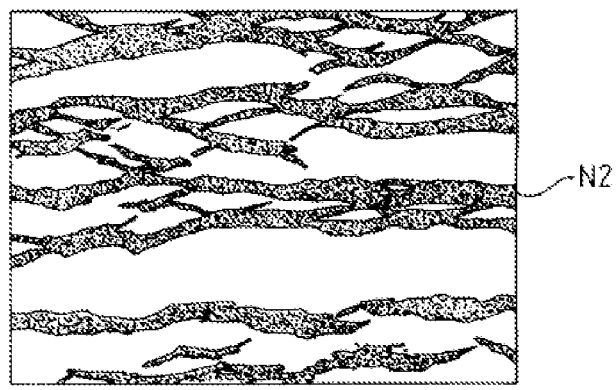
Figure 8:
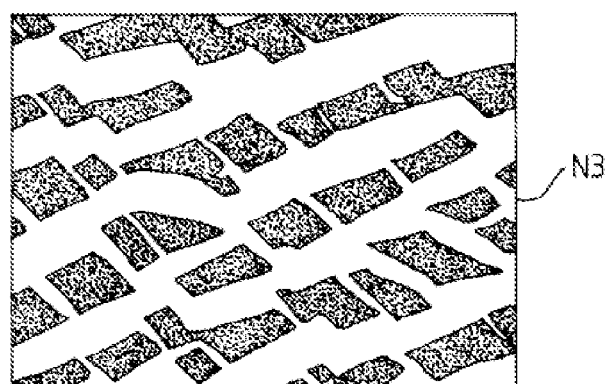
Figure 9:
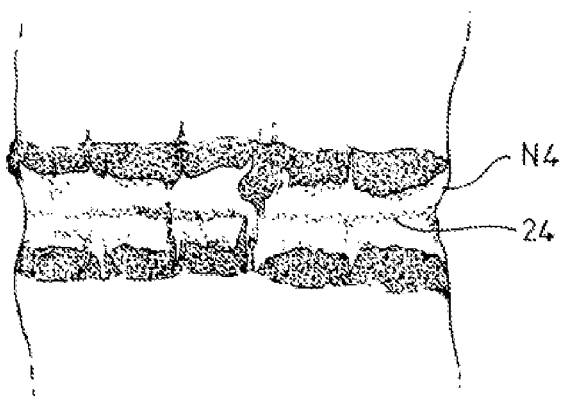

FIGS. 7 to 9 show, in a similar way to FIG. 6, portions of the internal surface of a tube showing increasing deterioration.

Figure 1:
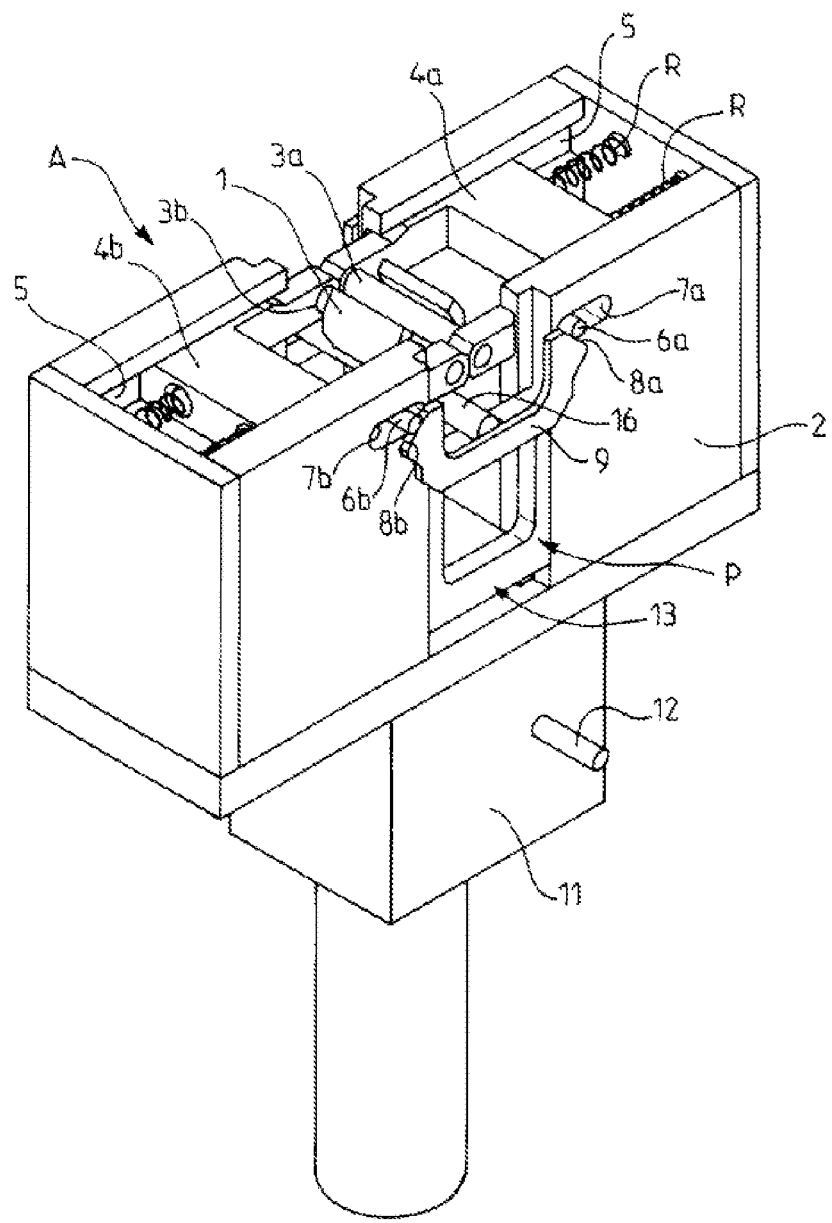
FIG. 1 is a perspective view of apparatus of the invention with the spreader bars moved one against the other and with a tube portion installed around them.

Referring to FIG. 1 of the drawings, there may be seen apparatus A for turning inside out a tube portion 1 open over an arc of its circumference. The portion 1 has the shape of an open ring extending over approximately three quarters of its circumference and open over substantially one quarter thereof. This portion 1 is taken from a plastic material pipe, notably a black polyethylene pipe for water distribution networks, and generally has an outside diameter from 20 mm to 50 mm, the thickness of this wall varying between 2 mm and 7 mm. This example is not limiting on the invention. The apparatus A may equally serve to turn inside out tube portions in another material, for example metal tube portions.

The apparatus A includes a frame 2 of rectangular parallelepiped shape the peripheral walls of which are vertical in the FIG. 1 representation. The frame is open at its top. By way of nonlimiting example, this frame may have a width of approximately 150 mm, a height of approximately 220 mm, and a depth of approximately 55 mm.

Two adjacent bars 3a, 3b are mounted to slide in the common plane of their geometrical axes, which is a horizontal plane in the FIG. 1 representation. Each bar 3a, 3b is carried, at its ends, by a branch of a stirrup-shaped support 4a, 4b mounted to slide in horizontal grooves 5 provided in the vertical longitudinal walls of the frame 2.

Compression springs R are provided between the transverse walls of the frame 2 and the facing face of the supports 4a, 4b in such a manner as to push these supports toward each other and to move the bars 3a, 3b closer to each other, which bars may come into contact with each other in the starting position.

The concave side of the open tube portion 1 may be engaged around the bars 3a, 3b when moved close to each other as shown in FIG. 1, the open arc of the portion 1 being oriented upward. The portion 1 is disposed so as to have the same vertical mediator plane as the set of bars 3a, 3b. Each support 4a, 4b is provided on its sides with a finger 6a, 6b passing through an oblong opening 7a, 7b provided in the large vertical faces of the frame 2. The fingers 6a, 6b project outward and come to bear against inclined ramps 8a, 8b of an upwardly facing U-shaped double cam 9 constituting spreader means. The ramps 8a, 8b converge in the upward direction so that raising the cam 9 causes movement apart of the fingers 6a, 6b, the supports 4a, 4b and the bars 3a, 3b. Fingers 6a, 6b and a cam 9 are provided on each side of the frame 2.

Pusher means P are provided and come to bear against the exterior convex area of the portion 1. The pusher means P comprise a rod 10 (FIGS. 2 and 3) orthogonal to the plane of the geometrical axes of the bars 3a, 3b and therefore vertical when the bars are disposed in a horizontal plane.

The rod 10 is moved vertically by force amplifier means 11, notably gears, in particular a worm gear. The force amplifier is actuated by driving in rotation a shaft 12 either by means of a crank or a wheel (not shown) actuated manually or by means of a motor, notably an electric motor (not shown).

A pusher 13, of double-stirrup or lantern shape, is fixed to the upper end of the rod 10. This pusher includes a base plate 14 (FIGS. 2 and 3) in which a central hole is provided through which passes a threaded end of the rod 10 for fixing the pusher 13 by means of a nut. Each lateral extremity of the plate 14 is fastened to a frame 15 (FIGS. 2 and 3) including a rectangular central opening situated in a plane parallel to the adjoining large vertical face of the frame. The upper horizontal edge of the frame 15 supports the end of an interchangeable cylindrical element 16 having its geometrical axis parallel to the bars 3a, 3b and constituting the pusher member as such. This cylindrical element 16 comes into contact with the portion 1, initially against its exterior generatrix equidistant from the ends of the open arc of the portion 1.

The apparatus advantageously includes a mobile observation device 17 (FIG. 4) with optical magnification means, in particular an eyepiece 18 with a counting square defining a unit surface area, for example of 3.1 mm$^2$. Within this square the observer may count a number of lines or elements characteristic of the area examined. The device 17 may include a mobile support casing 19 placed on the frame 2 of the apparatus. The eyepiece 18 is situated at the center of the upper face of the casing 19. The observation device 17, placed above the open upper face of the casing, enables examination of the internal surface of the tube portion turned inside out.

The observation device 17 may include a digital camera 20 the objective lens of which is held above, or in place of, the eyepiece 18, to capture digital photos of the examined internal surface of the tube portion turned inside out. The camera 20 is advantageously connected to image processing means 21 with software adapted to determine a degree of deterioration of the tube. Display means 22 are preferably provided and connected to the processing means 21 to view the images and/or the results.

This being so, the procedure for evaluating the deterioration of a polyethylene pipe in accordance with the invention is as follows.

In a laboratory, or in the field, there is taken from a polyethylene pipe to be examined a ring the axial length of which may be approximately 10 mm. The pipe generally has an outside diameter of 20 mm to 50 mm and a wall thickness that varies between 2 mm and 7 mm.

From the circular ring taken in this way there is cut out an arc of approximately one quarter turn to obtain a portion of open section extending over approximately three quarters of a turn.

Apparatus (not shown) is provided for producing the three quarter-turn ring. This apparatus is constituted of superposed conical templates over which the complete ring cut from the tube is threaded. Depending on the inside diameter of the tube, the complete ring stops at a greater or lesser height. Two blades at an angle of 90° to each other then cut off an open ring, extending over three quarter-turns, after the blades and the ring are brought manually into contact. Depending on the cleanliness of the internal wall of the pipe, the operator could be called upon to clean it using a cleaning wipe or a damp cloth.

The test piece formed by the three-quarter-turn ring constitutes the portion 1 that is then placed in the apparatus A of the invention. The bars 3a, 3b are in contact with each other and the portion 1 is disposed with its open part facing upward, as shown in FIG. 1. The cylindrical pusher member 16 is chosen so that its diameter is suited to the diameter and thickness of the portion 1.

The pusher means P are then actuated either manually or by a motor, not shown, in order to raise the rod 10, which pushes the cylindrical element 16 against the lower convex part of the portion 1 the ends of which are retained by the bars 3a, 3b. These bars move apart as the element 16 rises because of the cooperation of the ramps 8a, 8b with the fingers 6a, 6b.

The load applied by the horizontal cylindrical element 16 causes the ring of pipe to be turned inside out. The cylindrical element 16 is changeable according to the thickness of the wall of the tube. Turning the ring inside out is facilitated by the cams 9 which cause the two bars 3a, 3b to move apart at the start of the travel of the element 16. The vertical travel of the horizontal cylindrical element 16 is stopped by abutments (not shown) adjusted according to the diameter of the tube from which the portion 1 is taken. Because of the action of the return springs R, the two sliding bars 3a, 3b move the two outside edges of the ring closer together.

The conjugate action of the movement apart of the bars 3a, 3b and the cylindrical element 16 pushing against the outside surface of the portion 1 causes relative flattening of the portion 1 as shown in FIG. 2 followed by complete turning inside out. This portion 1 finds itself wound over substantially 180° onto the cylindrical element 16 in the shape of a staple, the exterior surface of which is then the internal surface of the portion 1.

The internal face of the portion 1 turned inside out may then be observed while it is still on the apparatus A.

The sample turned inside out in this way may be retained in this position with the aid of a horizontal U-shaped retaining member 22 engaged on either side of the branches of the portion 1 turned inside out to hold it in this state, after separation from the cylindrical element 16. A sample 23 as shown in FIG. 3 is then obtained that may be retained for complementary analysis.

The complete turning inside out of the pipe portion 1 is preferably effected at constant speed. The internal wall of the tube section, after turning it inside out, has a convex radius of curvature, whereas it had a concave radius of curvature before that operation. The radius of curvature of the external wall of the tube turned inside out is substantially equal to the radius of the cylindrical element 16 which is itself equal to at least twice the thickness of the wall of the section 1.

Once the turning inside out operation has been effected, the observation device 17 with magnification is placed above the internal surface of the tube portion 1. Top-up lighting integrated into the optical device facilitates observation. After the magnification system is focused, either a photograph of the internal wall may be taken or it may be observed with the naked eye.

To photograph the pattern of deterioration of the internal wall of the tube, the digital camera 20 is fixed to the observation device. The digital photograph produced is transferred into image processing software 21. The latter is designed to enable conversion to binary form of the photo that has been taken. This conversion to binary form is to distinguish weakened areas of the material from intact areas. On the basis of the objects in binary form obtained from the photograph, the software is able to measure the physical parameters that define them (for example: width, length, area, roughness, Feret diameter, etc.).

The results obtained are then transmitted to the display means 22, notably constituted by a spreadsheet. By studying the physical parameters defining the binary objects, this spreadsheet makes it possible to define by a process of dichotomy the intensity of the phenomenon of weakening of the internal wall of the polyethylene pipe under study, in particular on a scale of seven discrete levels running from a non-deteriorated state to a very highly deteriorated state.

Alternatively, it is possible to effect a visual assessment of the state of deterioration using a nomogram constituted by a set of reference photographs or representations, shown in FIGS. 5 to 9, enabling the level of deterioration of the tube to be evaluated on a scale including a plurality of discrete levels.

The operator identifies the level of deterioration of the tube under study by comparison with the nomogram.

The reference photographs in FIGS. 5 to 9 show an area of the internal wall of the pipe of approximately. The portion 1 turned inside out is observed with the aid of an eyepiece-type magnifying device including a counting square. By comparison with the representations of FIGS. 5 to 9, the intensity of the phenomenon of deterioration may be evaluated visually in terms of four levels by considering the number and the size of the black areas of polyethylene that have not deteriorated.

FIG. 5 corresponds to a nil deterioration level N0, with a single black area of polyethylene that has not deteriorated.

FIG. 6 corresponds to a deterioration level N1 that is characterized by the presence of more than 100 fragmented black areas less than 0.10 mm wide, corresponding to polyethylene that has not deteriorated in a rectangle with an area of 3.1 mm$^2$.

FIG. 7 corresponds to a deterioration level N2 having from 2 to 20 continuous black areas less than 0.2 mm wide.

FIG. 8 corresponds to a deterioration level N3 having from 20 to 100 fragmented black areas more than 0.2 mm wide corresponding to polyethylene that has not deteriorated.

Finally, FIG. 9 corresponds to a maximum deterioration level N4 that is characterized by the appearance of macrocracks in the form of a white area 24 oriented in the direction of the generatrices of the cylindrical area turned inside out.

On completion of comparing the area turned inside out with the nomogram of FIGS. 5 to 9, depending on the level of deterioration found, the operator may decide to renew or to repair the leaking pipe.

The operations described above, and FIGS. 5 to 9 constituting the nomogram, relate to a black polyethylene pipe. For different plastic materials the general indications given remain applicable but the areas that have not deteriorated will have colors in corresponding relationship to that of the plastic material concerned.

If the operator finds a deterioration level from N0 to N1, for example, it is not necessary to replace the pipe, but a simple repair could be effected.

If the deterioration level is equal to N2, replacement of the pipe in the relatively near future could be envisaged.

If the deterioration level is equal to N3 or N4, the pipe should be replaced without delay.

The apparatus and the method of the invention enable the condition of a pipe in which a leak has been found to be evaluated not only in the laboratory but also in the field.

As a preventive measure, such evaluations could be effected even before a leak occurs to determine if replacement of the pipes is to be envisaged in the near or distant future.

The invention claimed is:

1. An apparatus for the examination of the internal wall of a tube by turning inside out a tube portion the section of which is open over an arc of its circumference, in particular over approximately a quarter of its circumference, the apparatus comprising:

two adjacent parallel bars, mounted to slide in a frame and adapted to be moved in a plane of the bars, around which bars may be engaged the concave side of the open portion of the tube, with a geometrical axis of the tube being parallel to the bars, pusher means for pushing in a direction substantially orthogonal to the plane of the bars, adapted to come to bear against the exterior convex area of the tube portion, and spreader means adapted to move the bars apart in response to the pushing against the convex area of the tube portion, wherein the tube portion may be turned inside out on either side of the pushing area.

2. The apparatus as claimed in claim 1, wherein the pusher means comprises, in order to come into contact with the tube portion, an interchangeable cylindrical element, with a geometrical axis of the cylindrical element being parallel to the bars, disposed on the convex side of the tube portion opposite the bars, the cylindrical element being carried at each end by a pusher moved by a rod.

3. The apparatus as claimed in claim 2, wherein the diameter of the cylindrical element is at least equal to the thickness of the tube portion to be turned inside out.

4. The apparatus as claimed in claim 2, wherein the pusher means comprises a force amplifier for moving the cylindrical element against the tube portion.

5. The apparatus as claimed in claim 2, wherein the spreader means comprises a double cam adapted to cooperate with a sliding support associated with each bar, this cam being moved by the pusher of the pusher means to cause the bars to be moved apart when pushed.

6. The apparatus as claimed in claim 1, further comprising a mobile observation device with optical magnification means for observing the internal surface of the tube portion turned inside out.

7. The apparatus as claimed in claim 6, wherein the observation device includes a digital camera connected to image processing means with software adapted to determine a degree of deterioration of the tube.

8. A method of analyzing the level of deterioration of a tube formed of a plastic material, wherein a tube portion is taken from which an arc of its circumference is removed to open the section, wherein the open portion of the tube is turned inside out by the apparatus as claimed in claim 1 and the internal wall of the area turned inside out is observed to determine the level of deterioration of the tube.

9. The analysis method as claimed in claim 8, wherein the tube portion is turned inside out at a constant speed of movement of the pusher means.

10. The analysis method as claimed in claim 8, wherein the plastic material comprises to a black polyethylene tube, further comprising conducting a visual assessment of the deterioration according to a nomogram comprising a set of reference representations of tube portions turned inside out corresponding to various levels of deterioration (N0-N4).

11. The analysis method of claim 8, wherein the plastic material comprises polyethylene.

12. A method of producing a nomogram comprising a set of reference representations of tube portions corresponding to various levels of deterioration, the method comprising turning a plurality of tube portions inside out by the apparatus of claim 1, wherein an internal surface of each tube portion shows a different amount of deterioration as compared to the other tube portions;

creating the set of reference representations based on the inside out tube portions.

\* \* \* \* \*